United States Patent
Harada et al.

(10) Patent No.: US 10,745,331 B2
(45) Date of Patent: Aug. 18, 2020

(54) METHOD FOR PRODUCING GUERBET ALCOHOL

(71) Applicant: KAO CORPORATION, Tokyo (JP)

(72) Inventors: Shuji Harada, Wakayama (JP); Yuichi Ogasawara, Wakayama (JP); Shingo Takada, Wakayama (JP); Takenori Totoki, Izumisano (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/318,835

(22) PCT Filed: Jun. 26, 2017

(86) PCT No.: PCT/JP2017/023401
§ 371 (c)(1),
(2) Date: Jan. 18, 2019

(87) PCT Pub. No.: WO2018/016270
PCT Pub. Date: Jan. 25, 2018

(65) Prior Publication Data
US 2019/0284120 A1    Sep. 19, 2019

(30) Foreign Application Priority Data

Jul. 21, 2016   (JP) ................................ 2016-143644

(51) Int. Cl.
| | |
|---|---|
| *C07C 29/34* | (2006.01) |
| *B01J 23/44* | (2006.01) |
| *B01J 23/745* | (2006.01) |
| *C07C 31/02* | (2006.01) |
| *C07C 31/125* | (2006.01) |
| *C07B 61/00* | (2006.01) |

(52) U.S. Cl.
CPC .............. *C07C 29/34* (2013.01); *B01J 23/44* (2013.01); *B01J 23/745* (2013.01); *C07C 31/02* (2013.01); *C07C 31/125* (2013.01); *C07B 61/00* (2013.01)

(58) Field of Classification Search
CPC ................................ C07C 29/34; B01J 23/44
USPC ......................................................... 568/905
See application file for complete search history.

(56) References Cited

U.S. PATENT DOCUMENTS 2,457,866 A  *  1/1949  Carter ..................... C07C 29/34
                                                568/905
4,011,273 A      3/1977  Abend et al.

FOREIGN PATENT DOCUMENTS

| CN | 105646149 A | 6/2016 |
| EP | 0 299 720 A2 | 1/1989 |
| JP | 52-19605 | 2/1977 |
| JP | 64-34933 A | 2/1989 |
| JP | 6434933 A * | 2/1989 |
| JP | 3-279336 A | 12/1991 |
| JP | 4-502764 A | 5/1992 |

OTHER PUBLICATIONS

Guerbet, Compt. Rend., 128, 511 (1899), total 3 pages.
International Search Report, issued in PCT/JP2017/023401, dated Sep. 5, 2017.
Extended European Search Report, dated Feb. 12, 2020, for European Application No. 17830790.6.

* cited by examiner

*Primary Examiner* — Deborah D Carr
(74) *Attorney, Agent, or Firm* — Birch, Stewart, Kolasch & Birch, LLP

(57) ABSTRACT

To provide a method for producing a Guerbet alcohol without necessity of the use of a solvent, capable of enhancing the conversion and the yield. A method for producing a Guerbet alcohol, including the following steps 1 to 3 in this order: step 1: preparing a liquid composition containing an aliphatic alcohol and a base; step 2: holding the liquid composition at 100° C. or more and 180° C. or less to thereby adjust a water amount in the liquid composition to less than 0.28% by mass; and step 3: setting the liquid composition to be more than 180° C.

10 Claims, No Drawings

METHOD FOR PRODUCING GUERBET ALCOHOL

FIELD OF THE INVENTION

The present invention relates to a method for producing a Guerbet alcohol.

BACKGROUND OF THE INVENTION

A Guerbet alcohol is a branched alcohol obtained through dehydration condensation of an aliphatic alcohol. A Guerbet alcohol is a useful substance that is directly used in or used as an intermediate material in the fields including a surfactant, a textile oil, a softening agent, a cosmetic product, a medical drug, a lubricating oil, and the like.

As a method for preparing a Guerbet alcohol, a method of subjecting an aliphatic alcohol to self-condensation in the presence of a strong base represented by an alkali metal hydroxide at a high temperature of 200° C. or more has been known (see, for example, Compt. Rend., 128, 511 (1899) (NPL 1)). However, the known method is not preferred in terms of the reaction efficiency due to the low reaction rate. The Guerbet reaction is such a reaction that an alcoholate is formed from a raw material alcohol and a strong base, an aldehyde is formed through dehydrogenation of the raw material alcohol with the alcoholate functioning like a catalyst, two molecules of the aldehyde undergo aldol condensation and then are dehydrated to provide an unsaturated aldehyde, and then the unsaturated aldehyde thus formed is reduced to form a Guerbet alcohol. The reason of the low reaction rate of the known method is considered to be deactivation of the strong base as a catalyst through saponification thereof with the aldehyde or the unsaturated aldehyde with water by-produced in the formation of the alcoholate or the dehydration of the aldol. Accordingly, the reaction is generally performed while removing by-produced water under solvent reflux (see, for example, JP 3-279336 A (PTL 1)).

SUMMARY OF THE INVENTION

The present invention relates to a method for producing a Guerbet alcohol, including the following steps 1 to 3 in this order:

step 1: preparing a liquid composition containing an aliphatic alcohol and a base;
step 2: holding the liquid composition at 100° C. or more and 180° C. or less to thereby adjust a water amount in the liquid composition to less than 0.28% by mass; and
step 3: setting the liquid composition to be more than 180° C.

DETAILED DESCRIPTION OF THE INVENTION

The method of PTL 1 has a disadvantage that the solvent is necessarily isolated and removed after completing the reaction. For the reason, a method for producing a Guerbet alcohol without the use of a solvent is demanded.

The present invention relates to a method for producing a Guerbet alcohol without necessity of the use of a solvent, capable of enhancing the conversion and the yield.

The present inventors have found that the problem can be solved by holding the particular temperature range and decreasing the water content, in the temperature rising step in the reaction of an aliphatic alcohol in the presence of a base.

The method for producing a Guerbet alcohol of the present invention includes the following steps 1 to 3 in this order:

step 1: preparing a liquid composition containing an aliphatic alcohol and a base (which may be hereinafter referred to as a "reaction liquid")
step 2: holding the liquid composition at 100° C. or more and 180° C. or less to thereby adjusting a water amount in the liquid composition to be less than 0.28% by mass; and
step 3: setting the liquid composition to be more than 180° C.

Assuming that the aliphatic alcohol is represented by R—$CH_2$—$CH_2$—OH, the formation reaction of a Guerbet alcohol is shown by the following scheme.

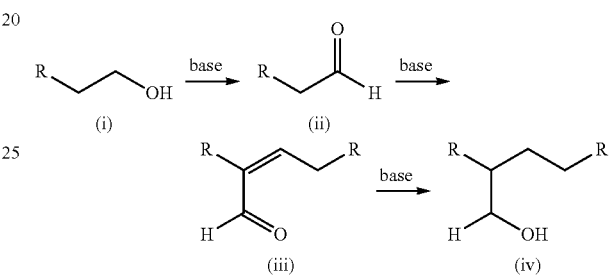

The aliphatic alcohol (i) is oxidized in the presence of the base to form an aldehyde (ii), and the aldehyde (ii) undergoes aldol condensation to form an aldehyde compound which is then reduced with the base to form a Guerbet alcohol (iv).

The major reaction is the reaction of from (i) to (iv) shown above, but in the case where, for example, KOH is used as the base, there is a problem that the aldehyde shown by the formula (ii) or (iii) is converted to a carboxylic acid with water present in the reaction system, and the carboxylic acid is saponified to form a compound shown by the formula (ii') or (iii'), resulting in deactivation of the base.

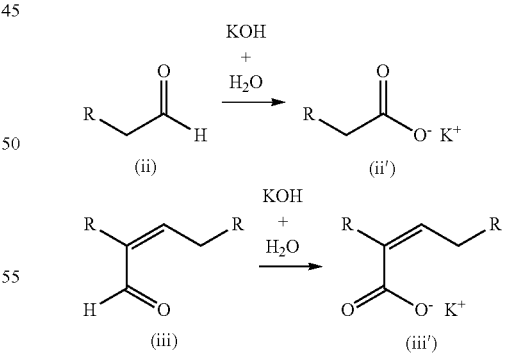

The invention described in PTL 1 has room for improvement from the standpoint of the economic efficiency and the productivity since the solvent is necessarily isolated and removed after completing the reaction.

In the present invention, in the reaction of an aliphatic alcohol in the presence of a base, the water amount at a temperature of 100° C. or more and 180° C. or less is brought less than 0.28% by mass. Specifically, in the present invention, in producing a Guerbet alcohol by using an aliphatic alcohol and a base at a temperature exceeding 180° C., in the temperature rising step, the liquid composition containing the aliphatic alcohol and the base (i.e., the reaction liquid) is held to 100° C. or more and 180° C. or less, and the water amount in the liquid composition is brought less than 0.28% by mass, and then the liquid composition is brought more than 180° C. It has been found that the deactivation of the base can be suppressed by the procedure, and a method for producing a Guerbet alcohol without the use of a solvent, capable of enhancing the conversion and the yield can be provided.

The detailed mechanism of the aforementioned effect is not clear, and a part thereof can be considered as follows. There is a problem that heating to more than 180° C. in the presence of a base, such as KOH, and water causes deactivation of the base through saponification, but in the present invention, it can be estimated that the formation of the alcoholate with the base, such as KOH, proceeds by holding the liquid composition to 100° C. or more and 180° C. or less, preferably 100° C. or more and 160° C. or less, and the amount of the base, such as KOH, itself present in the system and the amount of water present in the system, which are the cause of the problem, are sufficiently decreased by setting the water amount of the liquid composition to be less than 0.28% by mass, so as to suppress the deactivation of the basic catalyst, resulting in the enhancement of the conversion and the yield.

Step 1

The step 1 is a step of preparing a liquid composition containing an aliphatic alcohol and a base. It suffices that the preparation of the liquid composition is performed by mixing the components constituting the liquid composition, and is not particularly limited.

In the step 1, the liquid composition is preferably prepared under agitation, and the preferred embodiment of the power requirement for agitation may be the same as described for the step 2 later.

In the step 1, the temperature in preparing the liquid composition is preferably 5° C. or more, more preferably 10° C. or more, further preferably 15° C. or more, and still further preferably 20° C. or more, and is preferably less than 100° C., more preferably 80° C. or less, further preferably 60° C. or less, still further preferably 50° C. or less, still more further preferably 40° C. or less, and still more further preferably 30° C. or less, from the standpoint of the reaction equipment, the operability, and the production cost.

In the step 1, the pressure in preparing the liquid composition is not particularly limited, and is preferably ordinary pressure from the standpoint of the reaction equipment, the operability, and the production cost.

The components constituting the liquid composition will be described below.

Aliphatic Alcohol

In the present invention, the aliphatic alcohol as the raw material of the Guerbet alcohol may be saturated or unsaturated, may be straight-chain or branched, and may have a cyclic structure, and from the standpoint of the reactivity, the aliphatic alcohol is preferably a saturated aliphatic alcohol and preferably a straight-chain aliphatic alcohol, and more preferably a straight-chain saturated aliphatic alcohol. The aliphatic alcohol may be a primary alcohol or a secondary alcohol, and from the standpoint of the reactivity, the aliphatic alcohol is preferably a primary alcohol, more preferably a primary straight-chain aliphatic alcohol and more preferably a primary saturated aliphatic alcohol, and further preferably a primary straight-chain saturated aliphatic alcohol having a hydroxy group at the end of the hydrocarbon chain.

The number of carbon atoms of the aliphatic alcohol used in the present invention is preferably 6 or more, more preferably 8 or more, and further preferably 10 or more, and is preferably 22 or less, more preferably 18 or less, and further preferably 16 or less, from the standpoint of the reactivity.

The aliphatic alcohol may be used alone or as a combination of two or more kinds thereof.

The aliphatic alcohol is preferably one kind or two or more kinds selected from 1-hexanol, 1-heptanol, 1-octanol, 1-nonanol, 1-decanol, 1-undecanol, 1-dodecanol, 1-tridecanol, 1-tetradecanol, 1-pentadecanol, 1-hexadecanol, 1-heptadecanol, 1-octadecanol, 1-nonadecanol, 1-icosanol, 1-henicosanol, and 1-docosanol, more preferably one kind or two or more kinds selected from 1-octanol, 1-nonanol, 1-dodecanol, 1-tridecanol, 1-tetradecanol, 1-pentadecanol, 1-hexadecanol, 1-heptadecanol, and 1-octadecanol, and further preferably one kind or two or more kinds selected from 1-dodecanol, 1-tridecanol, 1-tetradecanol, 1-pentadecanol, and 1-hexadecanol, from the standpoint of the reactivity.

The amount of the aliphatic alcohol used in the present invention (i.e., the content of the aliphatic alcohol in the liquid composition) is preferably 90% by mass or more, more preferably 95% by mass or more, and further preferably the balance excluding the total amount of the base described later and water and/or a solvent arbitrarily contained in the liquid composition, from the standpoint of the productivity.

The aliphatic alcohol used in the present invention may contain water, and the water amount in the aliphatic alcohol is preferably 10% by mass or less, more preferably 1% by mass or less, further preferably 0.1% by mass or less, still further preferably 0.01% by mass or less, still more further preferably substantially no water contained, and still more further preferably 0% by mass, from the standpoint of decreasing the water content in the liquid composition.

The expression substantially no water contained means that the content of water is 0.001% by mass or less.

Base

In the present invention, the liquid composition contains a base.

Examples of the base include an inorganic base and an organic base.

Specific examples of the inorganic base include an alkali metal hydroxide, such as lithium hydroxide, sodium hydroxide, potassium hydroxide, rubidium hydroxide, and cesium hydroxide, an alkali metal carbonate, such as lithium carbonate, sodium carbonate, potassium carbonate, rubidium carbonate, and cesium carbonate, and an alkali metal hydrogen carbonate, such as lithium hydrogen carbonate, sodium hydrogen carbonate, potassium hydrogen carbonate, rubidium hydrogen carbonate, and cesium hydrogen carbonate. The inorganic base may be used as it is, and may be used in the form of an aqueous solution.

Examples of the organic base include an alkali metal alkoxide compound, such as methoxysodium, ethoxysodium, t-butoxysodium, methoxypotassium, ethoxypotassium, and t-butoxypotassium, and an alkali metal acetate salt, such as sodium acetate and potassium acetate.

Among these, the bases is preferably a base having relatively high basicity capable of performing the dehydrogenation reaction and the aldol condensation reaction, more preferably an alkali metal hydroxide, such as lithium hydroxide, sodium hydroxide, potassium hydroxide, rubidium hydroxide, and cesium hydroxide, or an alkali metal alkoxide compound, such as methoxysodium, ethoxysodium, t-butoxysodium, methoxypotassium, ethoxypotassium, and t-butoxypotassium, and from the standpoint of the versatility and the economic efficiency, further preferably sodium hydroxide, potassium hydroxide, methoxysodium, or t-butoxypotassium.

The amount of the base used in the present invention (i.e., the content of the base in the liquid composition) is preferably 0.3% by mol or more, more preferably 1.0% by mol or more, further preferably 2.0% by mol or more, still further preferably 2.5% by mol or more, and still more further preferably 2.8% by mol or more, from the standpoint of the reactivity, and is preferably 6.0% by mol or less, more preferably 4.5% by mol or less, further preferably 4.0% by mol or less, and still further preferably 3.2% by mol or less, from the standpoint of the suppression of the side reaction, based on the aliphatic alcohol as the raw material.

In the step 1, the liquid composition is preferably prepared by using the base in the form of an aqueous solution from the standpoint of the operability and the reactivity. In the case where the base is used in the form of an aqueous solution, the concentration of the base in the aqueous solution is not particularly limited, and is preferably 30% by mass or more, more preferably 35% by mass or more, further preferably 40% by mass or more, and still further preferably 45% by mass or more, and is preferably 70% by mass or less, more preferably 65% by mass or less, further preferably 60% by mass or less, and still further preferably 55% by mass or less, from the standpoint of the operability and the versatility.

Co-Catalyst

In the present invention, the liquid composition preferably further contains a co-catalyst. The co-catalyst contained may accelerate the progress of the dehydrogenation reaction of the aliphatic alcohol, and the conversion and the yield may be further enhanced.

The co-catalyst that can be used in the present invention includes a metal, such as aluminum, iron, cobalt, nickel, copper, ruthenium, rhodium, palladium, silver, and platinum (which may be hereinafter referred to as a metal catalyst). These may be used alone or as a mixture or a composite thereof. The metal (metal catalyst) may be used after supporting on a carrier.

Examples of the composite metal catalyst include copper-chromite, copper-nickel, copper-nickel-palladium, copper-nickel-ruthenium, copper-zinc, copper-zinc-ruthenium, zinc-chromite, and copper-iron-aluminum.

Examples of the carrier include silica, alumina, silica-alumina, diatomaceous earth, carbon, activated carbon, zirconia, ceria, titania, and natural and synthetic zeolite.

The supported amount of the metal (metal catalyst) on the carrier is preferably 1% by mass or more, more preferably 3% by mass or more, and further preferably 5% by mass or more, and is preferably 50% by mass or less, more preferably 40% by mass or less, further preferably 30% by mass or less, still further preferably 20% by mass or less, and still more further preferably 10% by mass or less, based on the total amount of the carrier and the metal catalyst, from the standpoint of the reactivity.

The amount of the co-catalyst used (i.e., the content of the co-catalyst in the liquid composition) is preferably 0.001% by mass or more, more preferably 0.002% by mass or more, further preferably 0.005% by mass or more, and still further preferably 0.01% by mass or more, from the standpoint of the reactivity, and is preferably 0.5% by mass or less, more preferably 0.3% by mass or less, further preferably 0.1% by mass or less, and still further preferably 0.05% by mass or less, from the standpoint of the suppression of the side reaction, based on the aliphatic alcohol as a raw material. The amount of the co-catalyst used means the total amount of the co-catalyst, and for example, in the case where a metal catalyst is supported on a carrier, means the total amount of the metal catalyst and the carrier.

Water Amount

The water amount of the liquid composition prepared in the step 1 is not particularly limited, is preferably 0.28% by mass or more, more preferably 0.3% by mass or more, further preferably 0.4% by mass or more, still further preferably 0.5% by mass or more, still more further preferably 0.6% by mass or more, and still more further preferably 0.7% by mass or more, from the standpoint of the reactivity, and is preferably 3.3% by mass or less, more preferably 2.0% by mass or less, further preferably 1.8% by mass or less, and still further preferably 1.2% by mass or less, from the standpoint of the suppression of the side reaction.

Solvent

In the present invention, the liquid composition may further contain a solvent other than the aliphatic alcohol and water described above.

The solvent is preferably a solvent that is soluble in the aliphatic alcohol and is hardly soluble in water. The expression soluble in the aliphatic alcohol means that the solubility in the aliphatic alcohol at 25° C. is 10 g/100 g or more. The solubility of the solvent used in the present invention in the aliphatic alcohol is preferably 30 g/100 g or more, more preferably 50 g/100 g or more, and further preferably 100 g/100 g or more.

The expression hardly soluble in water means that the solubility in water at 25° C. is 3 g/100 g or less, which is preferably 1 g/100 g or less, more preferably 0.1 g/100 g or less, and further preferably 0.01 g/100 g or less.

The solvent is preferably a hydrocarbon solvent having a boiling point under ordinary pressure of 75° C. or more and 200° C. or less, and is preferably a solvent that forms an azeotrope with water, or a solvent having a boiling point that is proximate to the boiling point of the aliphatic alcohol as a raw material. The expression that the boiling point of the solvent is proximate to the boiling point of the aliphatic alcohol means that the absolute value of the difference between the boiling points is preferably 20° C. or less, more preferably 10° C. or less, and further preferably 5° C. or less.

The solvent is preferably a solvent that is stable to the base and has low reactivity with the aliphatic alcohol as a raw material.

Specific examples of the solvent include an aromatic hydrocarbon solvent, such as benzene, xylene, and toluene, and an aliphatic hydrocarbon solvent, such as octane and decane.

The solvent may be used alone or as a combination of two or more kinds thereof.

The amount of the solvent used (i.e., the content of the solvent in the liquid composition) is preferably 5% by mass or less, more preferably 3% by mass or less, further preferably 1% by mass or less, still further preferably 0.01% by mass or less, still more further preferably substantially 0% by mass, and still more further preferably 0% by mass, based on the raw material alcohol, from the standpoint of the productivity.

Step 2

The step 2 is a step of holding the liquid composition prepared in the step 1 at 100° C. or more and 180° C. or less, and adjusting the water amount in the liquid composition to be less than 0.28% by mass.

Water Amount

In the present invention, the water amount in the liquid composition (reaction liquid) at 100° C. or more and 180° C. or less is less than 0.28% by mass, preferably 0.25% by mass or less, and more preferably 0.20% by mass or less, from the standpoint of the suppression of the deactivation of the base. The water amount in the reaction liquid at 100° C. or more and 180° C. or less is preferably substantially 0% by mass, and may be, for example, 0.001% by mass or more.

In the step 2, it suffices that the water amount in the liquid composition is less than 0.28% by mass at any point at 100° C. or more and 180° C. or less, and the water amount is preferably less than 0.28% by mass at 180° C.

In the present invention, the liquid composition is brought more than 180° C. in the step 3, and in the step 2, the water amount in the liquid composition may be less than 0.28% by mass immediately before the step 3 (i.e., at 180° C.), from the standpoint of the efficient production of a Guerbet alcohol.

Holding Temperature and Holding Time

For adjusting the water amount in the liquid composition to be less than 0.28% by mass, the liquid composition is held at 100° C. or more and 180° C. or less. The liquid composition is preferably held to 100° C. or more and 180° C. or less under heating (i.e., heated and held) from the standpoint of efficiently decreasing the water amount in the liquid composition.

The expression that the liquid composition is held to $X°$ C. or more and $Y°$ C. or less ($100 \leq X \leq Y \leq 180$) means that the temperature of the liquid composition is held at a temperature range of $X°$ C. or more and $Y°$ C. or less from the time when the temperature becomes $X°$ C. or more until the time when the temperature exceeds $Y°$ C. While embodiments of holding the temperature of the liquid composition are not particularly limited, the temperature of the liquid composition may be raised to a temperature of $Z°$ C. that is $X°$ C. or more and $Y°$ C. or less ($X \leq 5 \leq Y$), then held to a constant temperature of $Z°$ C., and then raised to $Y°$ C., the liquid composition may be gradually heated to from $X°$ C. to $Y°$ C. to hold the temperature of the liquid composition within a range of $X°$ C. or more and $Y°$ C. or less, and the rise and fall of the temperature within a range of $X°$ C. or more and $Y°$ C. or less may be performed once or more. Among these, from the standpoint of the operability, it is preferred that the temperature of the liquid composition is held at a constant temperature within the aforementioned temperature range, or the liquid composition is gradually heated to hold the temperature of the liquid composition within a range of $X°$ C. or more and $Y°$ C. or less, and it is more preferred that the temperature thereof is held at a constant temperature within the aforementioned temperature range. In the case where the temperature of the liquid composition is raised, decreased, or held for controlling the temperature within a temperature range of $X°$ C. or more and $Y°$ C. or less, there may be cases where the temperature deviates with respect to the target temperature, for example, overheating, but the deviation is regarded to be the target temperature. The range of the deviation of the temperature is not particularly limited, and the absolute value of the deviation is preferably 5° C. or less, more preferably 4° C. or less, further preferably 3° C. or less, still further preferably 2° C. or less, and still more further preferably 1° C. or less.

The temperature where the liquid composition is held is 100° C. or more, preferably 120° C. or more, more preferably 140° C. or more, and further preferably 145° C. or more, from the standpoint of the acceleration of the removal of water from the liquid composition, and is 180° C. or less, preferably 170° C. or less, more preferably 160° C. or less, further preferably 155° C. or less, and still further preferably 150° C. or less, from the standpoint of the suppression of the deactivation of the base.

In the case where the liquid composition is held to a constant temperature, the temperature where the liquid composition is held to a constant temperature is preferably 100° C. or more, more preferably 120° C. or more, further preferably 140° C. or more, and still further preferably 145° C. or more, from the standpoint of the acceleration of the removal of water from the liquid composition, and is preferably 180° C. or less, more preferably 170° C. or less, further preferably 160° C. or less, still further preferably 155° C. or less, and still more further preferably 150° C. or less, from the standpoint of the suppression of the deactivation of the base.

In the present invention, the water amount after holding at 100° C. or more and 180° C. or less is preferably less than 0.28% by mass. In the case where the formation reaction of a Guerbet alcohol does not occur at 100° C. or more and 180° C. or less, the liquid composition does not undergo formation of water, and thus it is considered that the water amount is decreased during the holding.

The step 2 is preferably a step of holding at 100° C. or more and 150° C. or less to thereby adjust the water content to be less than 0.28% by mass.

In the case where the water amount is 0.28% by mass or more after holding within the temperature range, it is preferred that the liquid composition is further held until the water amount becomes less than 0.28% by mass. In the case where the water amount after holding at the temperature range exceeds the aforementioned preferred range, it is more preferred that the liquid composition is further held to make the water amount within the preferred range.

The period of time where the temperature of the liquid composition is held within a temperature range of 100° C. or more and 180° C. or less is preferably 70 minutes or more, more preferably 90 minutes or more, and further preferably 110 minutes or more, from the standpoint of the acceleration of the removal of water from the liquid composition, and is preferably 6.2 hours or less, more preferably 4.2 hours or less, and further preferably 2.2 hours or less, from the standpoint of the productivity, while depending on the temperature range for holding, the use of the gas stream described later, and the like. The period of time where the temperature of the liquid composition is held within the temperature range herein means the total of the periods of time where the temperature of the liquid composition is in the temperature range, and in the case where there is a deviation in temperature, the period of the deviation is also included.

In the case where the temperature of the liquid composition is held to a constant temperature within a temperature range of 100° C. or more and 180° C. or less, the period of time where the temperature is held to the constant temperature is preferably 10 minutes or more, more preferably 30 minutes or more, and further preferably 50 minutes or more, from the standpoint of the acceleration of the removal of water from the liquid composition, and is preferably 5 hours or less, more preferably 3 hours or less, and further preferably 1 hour or less, from the standpoint of the productivity, while depending on the temperature range for holding, the use of the gas stream described later, and the like.

Other Factors

In the step 2, it is preferred that water is purposefully discharged outside the system for accelerating the removal of water from the liquid composition. For discharging water, the liquid composition is preferably held at 100° C. or more and 180° C. or less under a gas stream, and more preferably held at 100° C. or more and 180° C. or less under a nitrogen stream.

In the case where the liquid composition is held at 100° C. or more and 180° C. or less under a gas stream, the flow rate of the gas is preferably 0.00001 m/sec or more, more preferably 0.0001 m/sec or more, and further preferably 0.001 m/sec or more, from the standpoint of the acceleration of the removal of water from the liquid composition, and is preferably 1 m/sec or less, and more preferably 0.1 m/sec or less, from the standpoint of the economic efficiency. The flow rate of the gas herein is a superficial velocity defined by the value obtained by dividing the volume velocity of the gas in the reaction tank by the cross sectional area of the reaction tank.

In the step 2, the pressure where the liquid composition is held at 100° C. or more and 180° C. or less may be ordinary pressure, and may be reduced pressure for removing water in the liquid composition outside the system.

The liquid composition is preferably held at 100° C. or more and 180° C. or less under ordinary pressure from the standpoint of the reaction equipment, the operability, and the production cost.

In the step 2, the liquid composition is preferably held at 100° C. or more and 180° C. or less under agitation from the standpoint of the acceleration of the removal of water from the liquid composition, and the power requirement for agitation is preferably 0.01 kW/m$^3$ or more, more preferably 0.1 kW/m$^3$ or more, further preferably 0.3 kW/m$^3$ or more, and still further preferably 0.5 kW/m$^3$ or more, and is preferably 10 kW/m$^3$ or less, and more preferably 5 kW/m$^3$ or less, from the standpoint of the equipment cost. The power requirement for agitation can be calculated by Nagata's expression described in Kagaku Kogaku Binran (Chemical Engineering Handbook), 7th ed., pp. 338 to 342.

Step 3

The step 3 is a step of setting the liquid composition obtained in the step 2, which has a water amount less than 0.28% by mass at 180° C., to be more than 180° C. In the step 3, one molecule of the Guerbet alcohol and one molecule of water are formed from two molecules of the aliphatic alcohol.

Temperature of Liquid Composition

The temperature of the liquid composition in the step 3 may be appropriately determined in consideration of the boiling point of the aliphatic alcohol as a raw material, and is more than 180° C., preferably 190° C. or more, more preferably 200° C. or more, and further preferably 220° C. or more, from the standpoint of the securement of the sufficient reaction rate to provide a high reaction efficiency, and is preferably 290° C. or less, more preferably 270° C. or less, and further preferably 250° C. or less, from the standpoint of the suppression of the side reaction.

The temperature of the liquid composition in the steps before the step 3, which include the steps 1 and 2, is preferably 180° C. or less from the standpoint of the securement of a high reaction efficiency.

Pressure of Gas Phase in Contact with Liquid Composition

In the step 3, the pressure of the gas phase in contact with the liquid composition may be ordinary pressure, and may be reduced pressure for removing water in the liquid composition outside the system.

The reaction is preferably performed under ordinary pressure from the standpoint of the reaction equipment, the operability, and the production cost.

Reaction Time

The reaction time in the step 3 is generally 1 hour or more, and is preferably 20 hours or less, and more preferably 10 hours or less, from the standpoint of the productivity, while depending on the temperature of the liquid composition, the aliphatic alcohol as a raw material, and the like.

In the step 3, the reaction is preferably performed under agitation for performing the reaction efficiently, and the preferred embodiment of the power requirement for agitation may be the same as described for the step 2.

Reaction Equipment

The reaction equipment is preferably a batch type, and the material therefor may be stainless steel (such as SUS201, SUS202, SUS301, SUS302, SUS303, SUS304, SUS305, SUS316, SUS317, SUS329J1, SUS403, SUS405, SUS420, SUS430, SUS430LX, and SUS630) or may be glass.

Guerbet Alcohol

The Guerbet alcohol obtained by the method for producing a Guerbet alcohol of the present invention may be saturated or unsaturated, may be primary or secondary, and may have a cyclic structure, and a β-branched alcohol is preferred from the standpoint of the reactivity.

The number of carbon atoms of the Guerbet alcohol of the present invention is preferably 12 or more, more preferably 16 or more, and further preferably 20 or more, and is preferably 44 or less, more preferably 36 or less, and further preferably 32 or less, from the standpoint of the reactivity.

Examples of the Guerbet alcohol formed in the present invention include 2-decyl-1-tetradecanol, 2-hexyl-1-decanol, and 2-tetradecyl-1-octadecanol.

The Guerbet alcohol obtained by the method of the present invention may be purified depending on necessity by a distillation operation or the like, and may be applied as it is to various purposes. The Guerbet alcohol is useful as a raw material, an intermediate material, or the like of a surfactant, a textile oil, a softening agent, a cosmetic product, a medical drug, a lubricating oil, and the like. The Guerbet alcohol preferably has a purity of 95% by mass or more from the standpoint of these applications.

In relation to the aforementioned embodiments, the present invention further relates to the methods for producing a Guerbet alcohol shown below.

<1> A method for producing a Guerbet alcohol, including the following steps 1 to 3 in this order:

step 1: preparing a liquid composition containing an aliphatic alcohol and a base;

step 2: holding the liquid composition at 100° C. or more and 180° C. or less to thereby adjust a water amount in the liquid composition to be less than 0.28% by mass; and step 3: setting the liquid composition to be more than 180° C.

<2> The method for producing a Guerbet alcohol according to the item <1>, wherein in the step 1, the temperature in preparing the liquid composition is preferably 5° C. or more, more preferably 10° C. or more, further preferably 15° C. or more, and still further preferably 20° C. or more, and is preferably less than 100° C., more preferably 80° C. or less, further preferably 60° C. or less, still further preferably 50° C. or less, still more further preferably 40° C. or less, and still more further preferably 30° C. or less.

<3> The method for producing a Guerbet alcohol according to the item <1> or <2>, wherein in the step 1, the pressure in preparing the liquid composition is preferably ordinary pressure.

<4> The method for producing a Guerbet alcohol according to any one of the items <1> to <3>, wherein the aliphatic alcohol is preferably a primary aliphatic alcohol, preferably a saturated aliphatic alcohol, preferably a straight-chain aliphatic alcohol, more preferably a straight-chain saturated aliphatic alcohol, more preferably a primary straight-chain aliphatic alcohol, more preferably a primary saturated aliphatic alcohol, and further preferably a primary straight-chain saturated aliphatic alcohol having a hydroxy group at the end of the hydrocarbon chain.

<5> The method for producing a Guerbet alcohol according to any one of the items <1> to <4>, wherein the number of carbon atoms of the aliphatic alcohol is preferably 6 or more, more preferably 8 or more, and further preferably 10 or more, and is preferably 22 or less, more preferably 18 or less, and further preferably 16 or less.

<6> The method for producing a Guerbet alcohol according to any one of the items <1> to <5>, wherein the aliphatic alcohol is a saturated aliphatic alcohol having a number of carbon atoms of 6 or more and 22 or less.

<7> The method for producing a Guerbet alcohol according to any one of the items <1> to <6>, wherein the aliphatic alcohol is used alone or as a combination of two or more kinds thereof.

<8> The method for producing a Guerbet alcohol according to any one of the items <1> to <7>, wherein the water amount in the aliphatic alcohol is preferably 10% by mass or less, more preferably 1% by mass or less, further preferably 0.1% by mass or less, still further preferably 0.01% by mass or less, still more further preferably substantially no water contained, and still more further preferably 0% by mass.

<9> The method for producing a Guerbet alcohol according to any one of the items <1> to <8>, wherein the base is preferably a base having relatively high basicity capable of performing the dehydrogenation reaction and the aldol condensation reaction, more preferably one or more selected from the group consisting of an alkali metal hydroxide, such as lithium hydroxide, sodium hydroxide, potassium hydroxide, rubidium hydroxide, and cesium hydroxide, and an alkali metal alkoxide compound, such as methoxysodium, ethoxysodium, t-butoxysodium, methoxypotassium, ethoxypotassium, and t-butoxypotassium, and further preferably one or more selected from the group consisting of sodium hydroxide, potassium hydroxide, methoxysodium, or t-butoxypotassium.

<10> The method for producing a Guerbet alcohol according to any one of the items <1> to <9>, wherein the amount of the base is preferably 0.3% by mol or more, more preferably 1.0% by mol or more, further preferably 2.0% by mol or more, still further preferably 2.5% by mol or more, and still more further preferably 2.8% by mol or more, and is preferably 6.0% by mol or less, more preferably 4.5% by mol or less, further preferably 4.0% by mol or less, and still further preferably 3.2% by mol or less, based on the aliphatic alcohol.

<11> The method for producing a Guerbet alcohol according to any one of the items <1> to <10>, wherein in the step 1, the base is preferably used in the form of an aqueous solution.

<12> The method for producing a Guerbet alcohol according to the item <11>, wherein the concentration of the base in the aqueous solution is preferably 30% by mass or more, more preferably 35% by mass or more, further preferably 40% by mass or more, and still further preferably 45% by mass or more, and is preferably 70% by mass or less, more preferably 65% by mass or less, further preferably 60% by mass or less, and still further preferably 55% by mass or less.

<13> The method for producing a Guerbet alcohol according to any one of the items <1> to <12>, wherein the liquid composition preferably further contains a co-catalyst.

<14> The method for producing a Guerbet alcohol according to the item <13>, wherein the co-catalyst used is preferably a metal (metal catalyst) selected from the group consisting of aluminum, iron, cobalt, nickel, copper, ruthenium, rhodium, palladium, silver, and platinum, or a mixture or a composite of the metal.

<15> The method for producing a Guerbet alcohol according to the item <14>, wherein the composite metal catalyst is preferably one or more selected from the group consisting of copper-chromite, copper-nickel, copper-nickel-palladium, copper-nickel-ruthenium, copper-zinc, copper-zinc-ruthenium, zinc-chromite, and copper-iron-aluminum.

<16> The method for producing a Guerbet alcohol according to any one of the items <13> to <15>, wherein the co-catalyst is preferably the metal catalyst supported on a carrier.

<17> The method for producing a Guerbet alcohol according to the item <16>, wherein the carrier is preferably selected from the group consisting of silica, alumina, silica-alumina, diatomaceous earth, carbon, activated carbon, zirconia, ceria, titania, and natural and synthetic zeolite.

<18> The method for producing a Guerbet alcohol according to the item <16> or <17>, wherein the supported amount of the metal catalyst on the carrier is preferably 1% by mass or more, more preferably 3% by mass or more, and further preferably 5% by mass or more, and is preferably 50% by mass or less, more preferably 40% by mass or less, further preferably 30% by mass or less, still further preferably 20% by mass or less, and still more further preferably 10% by mass or less, based on the total amount of the carrier and the metal catalyst.

<19> The method for producing a Guerbet alcohol according to any one of the items <16> to <18>, wherein the amount of the co-catalyst used is preferably 0.001% by mass or more, more preferably 0.002% by mass or more, further preferably 0.005% by mass or more, and still further preferably 0.01% by mass or more, and is preferably 0.5% by mass or less, more preferably 0.3% by mass or less, further preferably 0.1% by mass or less, and still further preferably 0.05% by mass or less, based on the aliphatic alcohol as a raw material.

<20> The method for producing a Guerbet alcohol according to any one of the items <1> to <19>, wherein the water amount of the liquid composition prepared in the step 1 is preferably 0.28% by mass or more, more preferably 0.3% by mass or more, further preferably 0.4% by mass or more, still further preferably 0.5% by mass or more, still more further preferably 0.6% by mass or more, and still more further preferably 0.7% by mass or more, and is preferably 3.3% by mass or less, more preferably 2.0% by mass or less, further preferably 1.8% by mass or less, and still further preferably 1.2% by mass or less.

<21> The method for producing a Guerbet alcohol according to any one of the items <1> to <20>, wherein in the step 2, the water amount in the liquid composition at 100° C. or more and 180° C. or less is less than 0.28% by mass, preferably 0.25% by mass or less, more preferably 0.20% by mass or less, and further preferably substantially 0% by mass, and may be, for example, 0.001% by mass or more.

<22> The method for producing a Guerbet alcohol according to any one of the items <1> to <21>, wherein in the step 2, it is preferred that the liquid composition is held to a constant temperature of $Z°$ C. that is $X°$ C. or more and $Y°$ C. or less ($X \le Z \le Y$) ($100 \le X \le Y \le 180$), or gradually heated to from $X°$ C. to $Y°$ C. to hold within a range of $X°$ C. or more and Y° C. or less, or the rise and fall of the temperature within a range of X° C. or more and Y° C. or less is performed once or more, it is more preferred that the liquid composition is held to a constant temperature of Z° C., or gradually heated to hold to within a range of X° C. or more and Y° C. or less, and it is further preferred that the liquid composition is held to a constant temperature of Z° C.

<23> The method for producing a Guerbet alcohol according to any one of the items <1> to <22>, wherein in the step 2, the temperature where the liquid composition is held is 100° C. or more, preferably 120° C. or more, more preferably 140° C. or more, and further preferably 145° C. or more, and is 180° C. or less, preferably 170° C. or less, more preferably 160° C. or less, further preferably 155° C. or less, and still further preferably 150° C. or less.

<24> The method for producing a Guerbet alcohol according to any one of the items <1> to <23>, wherein in the step 2, the period of time where the temperature of the liquid composition is held at a temperature range of 100° C. or more and 180° C. or less is preferably 70 minutes or more, more preferably 90 minutes or more, and further preferably 110 minutes or more, and is preferably 6.2 hours or less, more preferably 4.2 hours or less, and further preferably 2.2 hours or less.

<25> The method for producing a Guerbet alcohol according to any one of the items <1> to <24>, wherein in the step 2, in the case where the temperature of the liquid composition is held to a constant temperature within a temperature range of 100° C. or more and 180° C. or less, the period of time where the temperature is held to the constant temperature is preferably 10 minutes or more, more preferably 30 minutes or more, and further preferably 50 minutes or more, and is preferably 5 hours or less, more preferably 3 hours or less, and further preferably 1 hours or less.

<26> The method for producing a Guerbet alcohol according to any one of the items <1> to <25>, wherein in the step 2, water is preferably intentionally discharged outside the system, and the liquid composition is preferably held at 100° C. or more and 180° C. or less under a gas stream, and more preferably held at 100° C. or more and 180° C. or less under a nitrogen stream.

<27> The method for producing a Guerbet alcohol according to any one of the items <1> to <26>, wherein in the step 2, the liquid composition is held at 100° C. or more and 180° C. or less under a gas stream, and the flow rate of the gas is preferably 0.00001 m/sec or more, more preferably 0.0001 m/sec or more, and further preferably 0.001 m/sec or more, and is preferably 1 m/sec or less, and more preferably 0.1 m/sec or less.

<28> The method for producing a Guerbet alcohol according to any one of the items <1> to <27>, wherein in the step 2, the pressure where the liquid composition is held at 100° C. or more and 180° C. or less may be ordinary pressure or reduced pressure, and preferably ordinary pressure.

<29> The method for producing a Guerbet alcohol according to any one of the items <1> to <28>, wherein in the step 2, the liquid composition is preferably held at 100° C. or more and 180° C. or less under agitation, and the power requirement for agitation is preferably 0.01 kW/m$^3$ or more, more preferably 0.1 kW/m$^3$ or more, further preferably 0.3 kW/m$^3$ or more, and still further preferably 0.5 kW/m$^3$ or more, and is preferably 10 kW/m$^3$ or less, and more preferably 5 kW/m$^3$ or less.

<30> The method for producing a Guerbet alcohol according to any one of the items <1> to <29>, wherein in the step 3, the temperature of the liquid composition is more than 180° C., preferably 190° C. or more, more preferably 200° C. or more, and further preferably 220° C. or more, and is preferably 290° C. or less, more preferably 270° C. or less, and further preferably 250° C. or less.

<31> The method for producing a Guerbet alcohol according to any one of the items <1> to <30>, wherein in the step 3, the pressure of the gas phase in contact with the liquid composition may be ordinary pressure or reduced pressure, and preferably ordinary pressure.

<32> The method for producing a Guerbet alcohol according to any one of the items <1> to <31>, wherein in the step 3, the reaction time may be 1 hour or more, and is preferably 20 hours or less, and more preferably 10 hours or less.

<33> The method for producing a Guerbet alcohol according to any one of the items <1> to <32>, wherein in the step 3, the liquid composition is preferably held at more than 180° C. under agitation, and the power requirement for agitation is preferably 0.01 kW/m$^3$ or more, more preferably 0.1 kW/m$^3$ or more, further preferably 0.3 kW/m$^3$ or more, and still further preferably 0.5 kW/m$^3$ or more, and is preferably 10 kW/m$^3$ or less, and more preferably 5 kW/m$^3$ or less.

<34> The method for producing a Guerbet alcohol according to any one of the items <1> to <33>, wherein the reaction equipment used in the steps 2 and 3 is preferably a batch type, and the material therefor may be stainless steel or glass.

<35> The method for producing a Guerbet alcohol according to the item <34>, wherein the stainless steel is selected from SUS201, SUS202, SUS301, SUS302, SUS303, SUS304, SUS305, SUS316, SUS317, SUS329J1, SUS403, SUS405, SUS420, SUS430, SUS430LX, and SUS630.

<36> The method for producing a Guerbet alcohol according to any one of the items <1> to <35>, wherein the Guerbet alcohol is a n-branched alcohol.

<37> The method for producing a Guerbet alcohol according to any one of the items <1> to <36>, wherein the number of carbon atoms of the Guerbet alcohol is preferably 12 or more, more preferably 16 or more, and further preferably 20 or more, and is preferably 44 or less, more preferably 36 or less, and further preferably 32 or less.

<38> The method for producing a Guerbet alcohol according to any one of the items <1> to <37>, wherein the liquid composition further contains a solvent.

<39> The method for producing a Guerbet alcohol according to the item <38>, wherein the solvent is soluble in the aliphatic alcohol and is hardly soluble in water.

<40> The method for producing a Guerbet alcohol according to the item <38> or <39>, wherein the solvent is a hydrocarbon solvent having a boiling point under ordinary pressure of 75° C. or more and 200° C. or less.

<41> The method for producing a Guerbet alcohol according to any one of the items <38> to <40>, wherein the solvent is a solvent that forms an azeotrope with water, or a solvent having a boiling point that is proximate to the boiling point of the aliphatic alcohol.

<42> The method for producing a Guerbet alcohol according to any one of the items <38> to <41>, wherein the solvent is selected from benzene, xylene, toluene, octane, and decane.

<43> The method for producing a Guerbet alcohol according to any one of the items <38> to <42>, wherein the amount of the solvent used is preferably 5% by mass or less, more preferably 3% by mass or less, further preferably 1% by mass or less, still further preferably 0.01% by mass or less, still more further preferably substantially 0% by mass, and still more further preferably 0% by mass, based on the aliphatic alcohol.

EXAMPLES

In Examples and Comparative Examples below, the percentage means percentage by mass unless otherwise indicated.

Example 1

Step 1: In a 1 L five-neck glass flask having one middle tube and four side tubes, 600.0 g (3.22 mol) of 1-dodecanol (produced by Kao Corporation, product name: Kalcol 2098), 11.3 g of a 48% potassium hydroxide aqueous solution (produced by Kanto Chemical Co., Inc.) as a base catalyst (potassium hydroxide: 0.16 mol/kg·1-dodecanol, 3.0% by mol based on 1-dodecanol), and 0.06 g of Cu—Fe—Al (produced by JGC Catalysts and Chemicals Ltd., product name: N2A3) as a co-catalyst (0.01% by mass based on 1-dodecanol) were charged, and the temperature was started to raise at 70° C./hr under agitation. The temperature at the start of agitation was 25° C.

An agitation bar having agitation blades was inserted in the middle tube of the five-neck flask, and the agitation bar was rotated with a motor to perform agitation. Among the four side tubes, a temperature sensor was inserted to one of the side tubes so as to be inserted into the liquid in the flask, an introduction tube for flowing nitrogen was inserted to another one of the side tubes, a hose pipe for discharging nitrogen and water outside the system was inserted to another one of the side tubes, and a sampling tube was inserted to another one of the side tubes. The temperature was raised with a mantle heater.

Step 2: At the time when the temperature of the reaction liquid reached 150° C., the temperature rise was temporarily terminated, and the reaction liquid is agitated at 150° C. for 30 minutes under a nitrogen stream, so as to remove water in the reaction liquid outside the system. Immediately after temporarily terminating the temperature rise, the liquid temperature was raised to 151° C. due to overheating, but was held to 150° C. thereafter. Herein, the temperature, at which the temperature rise is terminated, and the reaction liquid is agitated for a prescribed time, is referred to as a constant holding temperature, and the prescribed agitation time is referred to as a constant holding time. The constant holding temperature herein is 150° C., and the constant holding time is 30 minutes. The water amount in the reaction liquid measured at this time was as shown in the column of the water amount after holding at constant temperature in Table 1. Thereafter, the temperature was again raised at 70° C./hr under a nitrogen stream, and the water amount in the reaction liquid measured at the time when the temperature reached 180° C. was as shown in the column of the water amount at 180° C. in Table 1.

Step 3: Subsequently, the temperature was again raised at 70° C./hr under a nitrogen stream, and from the time when the temperature reached 240° C., the reaction was performed for 3 hours.

In the steps 1, 2, and 3, the power requirement for agitation was 1.2 kW/m$^3$. The superficial velocity in the step 2 was 5.4×10$^{-4}$ m/sec. The superficial velocity in the step 3 was 3.1×10$^{-6}$ m/sec.

The water amount in the reaction solution was quantitatively determined by analyzing with 870KF Titorino plus (produced by Metrohm AG) according to JIS K0068:2001.

The solution after completing the reaction was diluted with hexane, and analyzed by gas chromatography (column: Ultra-alloy capillary column 30.0 m×250 μm (produced by Frontier Laboratories, Ltd.), detector: FID, injection temperature: 300° C., detector temperature: 300° C., He flow rate: 4.6 mL/min), thereby quantitatively determining the product.

The conversion of the raw material alcohol (raw material alcohol conversion) and the yield of the Guerbet alcohol (Guerbet alcohol yield) thus obtained are shown in Table 1.

The raw material alcohol conversion and the Guerbet alcohol yield were calculated by the following expressions.

Raw material alcohol conversion (%)=100−(residual alcohol amount (mol)/charged amount of raw material alcohol (mol))×100

Guerbet alcohol yield (%)=(amount of Guerbet alcohol formed (mol)×2/charged amount of raw material alcohol (mol))×100

Comparative Example 1-1

The reaction was performed in the same manner as in Example 1 except that the temperature rise was performed without temporal termination, i.e., the time of holding at a constant temperature (constant holding time) was 0 minute, and the raw material alcohol conversion and the Guerbet alcohol yield were quantitatively determined. The results are shown in Table 1.

Comparative Example 1-2

The reaction was performed in the same manner as in Example 1 except that the time of holding at a constant temperature (constant holding time) was 10 minutes, and the raw material alcohol conversion and the Guerbet alcohol yield were quantitatively determined. The results are shown in Table 1.

TABLE 1

|  | Example 1 | Comparative Example 1-1 | Comparative Example 1-2 |
|---|---|---|---|
| Raw material alcohol | 1-dodecanol | 1-dodecanol | 1-dodecanol |
| Co-catalyst | Cu—Fe—Al | Cu—Fe—Al | Cu—Fe—Al |
| Co-catalyst amount (% by mass) | 0.01 | 0.01 | 0.01 |
| Constant holding temperature (° C.) | 150 | — | 150 |
| Constant holding time (min) | 30 | 0 | 10 |
| Water amount after holding at constant temperature (% by mass) | 0.15 | — | 0.32 |
| Holding time at 100° C. or more and 180° C. or less (min) | 98.6 | 68.6 | 78.6 |
| Water amount at 180° C. (% by mass) | 0.12 | 0.34 | 0.28 |
| Reaction temperature (° C.) | 240 | 240 | 240 |
| Reaction time (hr) | 3 | 3 | 3 |
| Raw material alcohol conversion (%) | 38 | 22 | 27 |
| Guerbet alcohol yield (%) | 32 | 18 | 22 |

Example 2-1

The reaction was performed in the same manner as in Example 1 except that the constant holding temperature in the step 2 was 100° C., the time of holding at a constant temperature (constant holding time) was 120 minutes, and the reaction time in the step 3 was 4 hours, and the raw material alcohol conversion and the Guerbet alcohol yield were quantitatively determined. The results are shown in Table 2.

Example 2-2

The reaction was performed in the same manner as in Example 1 except that the constant holding temperature in the step 2 was 120° C., and the reaction time in the step 3 was 4 hours, and the raw material alcohol conversion and the Guerbet alcohol yield were quantitatively determined. The results are shown in Table 2.

4 hours, and the raw material alcohol conversion and the Guerbet alcohol yield were quantitatively determined. The results are shown in Table 2.

Comparative Example 2-2

The reaction was performed in the same manner as in Example 2-3 except that instead of the step 2 of Example 2-3, the temperature rise was temporarily terminated at the time when the temperature of the reaction liquid reached 200° C., and the reaction liquid was agitated at 200° C. for 30 minutes under a nitrogen stream, and the raw material alcohol conversion and the Guerbet alcohol yield were quantitatively determined. The results are shown in Table 2.

TABLE 2

|  | Example 2-1 | Example 2-2 | Example 2-3 | Example 2-4 | Example 2-5 | Comparative Example 2-1 | Comparative Example 2-2 |
| --- | --- | --- | --- | --- | --- | --- | --- |
| Raw material alcohol | 1-dodecanol | 1-dodecanol | 1-dodecanol | 1-dodecanol | 1-dodecanol | 1-dodecanol | 1-dodecanol |
| Co-catalyst | Cu—Fe—Al | Cu—Fe—Al | Cu—Fe—Al | Cu—Fe—Al | Cu—Fe—Al | Cu—Fe—Al | Cu—Fe—Al |
| Co-catalyst amount (% by mass) | 0.01 | 0.01 | 0.01 | 0.01 | 0.01 | 0.01 | 0.01 |
| Constant holding temperature (° C.) | 100 | 120 | 150 | 160 | 170 | — | 200 |
| Constant holding time (min) | 120 | 30 | 30 | 30 | 30 | 0 | 30 |
| Water amount after holding at constant temperature (% by mass) | 0.23 | 0.30 | 0.15 | 0.14 | 0.05 | — | 0.03 |
| Holding time at 100° C. or more and 180° C. or less (min) | 188.6 | 98.6 | 98.6 | 98.6 | 98.6 | 68.6 | 68.6 |
| Water amount at 180° C. (% by mass) | 0.16 | 0.25 | 0.12 | 0.15 | 0.05 | 0.34 | 0.39 |
| Reaction temperature (° C.) | 240 | 240 | 240 | 240 | 240 | 240 | 240 |
| Reaction time (hr) | 4 | 4 | 4 | 4 | 4 | 4 | 4 |
| Raw material alcohol conversion (%) | 53 | 55 | 48 | 41 | 36 | 29 | 25 |
| Guerbet alcohol yield (%) | 47 | 51 | 42 | 36 | 31 | 24 | 20 |

Example 2-3

The reaction was performed in the same manner as in Example 1 except that the reaction time in the step 3 was 4 hours, and the raw material alcohol conversion and the Guerbet alcohol yield were quantitatively determined. The results are shown in Table 2.

Example 2-4

The reaction was performed in the same manner as in Example 2-3 except that the constant holding temperature in the step 2 was 160° C., and the raw material alcohol conversion and the Guerbet alcohol yield were quantitatively determined. The results are shown in Table 2.

Example 2-5

The reaction was performed in the same manner as in Example 2-3 except that the constant holding temperature in the step 2 was 170° C., and the raw material alcohol conversion and the Guerbet alcohol yield were quantitatively determined. The results are shown in Table 2.

Comparative Example 2-1

The reaction was performed in the same manner as in Comparative Example 1-1 except that the reaction time was Example 3

The reaction was performed in the same manner as in Example 2-3 except that 0.60 g of 5% Pd-supported carbon having a water content of 50% (produced by N.E. Chemcat Corporation) (catalyst amount including carrier: 0.05% by mass based on 1-dodecanol) was used as a co-catalyst instead of Cu—Fe—Al, and the raw material alcohol conversion and the Guerbet alcohol yield were quantitatively determined. The results are shown in Table 3.

Comparative Example 3

The reaction was performed in the same manner as in Example 2-3 except that the temperature rise was performed without temporal termination, i.e., the time of holding at a constant temperature (constant holding time) was 0 minute, and the raw material alcohol conversion and the Guerbet alcohol yield were quantitatively determined. The results are shown in Table 3.

TABLE 3

|  | Example 3 | Comparative Example 3 |
| --- | --- | --- |
| Raw material alcohol | 1-dodecanol | 1-dodecanol |
| Co-catalyst | Pd/C | Pd/C |
| Co-catalyst amount (% by mass) | 0.05 | 0.05 |
| Constant holding temperature (° C.) | 150 | — |
| Constant holding time (min) | 30 | 0 |
| Water amount after holding at constant temperature (% by mass) | 0.21 | — |

TABLE 3-continued

|  | Example 3 | Comparative Example 3 |
|---|---|---|
| Holding time at 100° C. or more and 180° C. or less (min) | 98.6 | 68.6 |
| Water amount at 180° C. (% by mass) | 0.26 | 0.36 |
| Reaction temperature (° C.) | 240 | 240 |
| Reaction time (hr) | 4 | 4 |
| Raw material alcohol conversion (%) | 72 | 62 |
| Guerbet alcohol yield (%) | 52 | 43 |

In Example 3, it was estimated that the water content at 180° C. was increased as compared to the water amount after holding at the constant temperature since the reaction proceeded slightly to form water in holding the temperature to 150° C. or in the temperature rise to from 150° C. or more and 180° C. or less, due to the high reactivity of the co-catalyst. Even in this case, the raw material alcohol conversion and the Guerbet alcohol yield can be enhanced by the liquid composition having the water amount less than 0.28% by mass at any point at 100° C. or more and 180° C. or less. In the present invention, the water amount at 180° C. is preferably less than 0.28% by mass.

Example 4

The reaction was performed in the same manner as in Example 2-3 except that by using the same equipment as in Example 1, 600.0 g (4.61 mol) of 1-octanol (produced by Kao Corporation, product name: Kalcol 0898), 16.2 g of a 48% potassium hydroxide aqueous solution (produced by Kanto Chemical Co., Inc.) as a base catalyst (potassium hydroxide: 0.23 mol/kg·1-octanol, 3.0% by mol based on 1-octanol), and 0.30 g of Cu—Fe—Al (produced by JGC Catalysts and Chemicals Ltd., product name: N2A3) as a co-catalyst (0.05% by mass based on 1-dodecanol) were charged, and in the step 2, the time of holding at a constant temperature (constant holding time) was 60 minutes, and the raw material alcohol conversion and the Guerbet alcohol yield were quantitatively determined. The results are shown in Table 4.

Comparative Example 4

The reaction was performed in the same manner as in Example 4 except that the temperature rise was performed without temporal termination, i.e., the time of holding at a constant temperature (constant holding time) was 0 minute, and the raw material alcohol conversion and the Guerbet alcohol yield were quantitatively determined. The results are shown in Table 4.

TABLE 4

|  | Example 4 | Comparative Example 4 |
|---|---|---|
| Raw material alcohol | 1-octanol | 1-octanol |
| Co-catalyst | Cu—Fe—Al | Cu—Fe—Al |
| Co-catalyst amount (% by mass) | 0.05 | 0.05 |
| Constant holding temperature (° C.) | 150 | — |
| Constant holding time (min) | 60 | 0 |
| Water amount after holding at constant temperature (% by mass) | 0.16 | — |
| Holding time at 100° C. or more and 180° C. or less (min) | 128.6 | 68.6 |
| Water amount at 180° C. (% by mass) | 0.05 | 0.45 |
| Reaction temperature (° C.) | 190 | 190 |
| Reaction time (hr) | 4 | 4 |

TABLE 4-continued

|  | Example 4 | Comparative Example 4 |
|---|---|---|
| Raw material alcohol conversion (%) | 25 | 14 |
| Guerbet alcohol yield (%) | 15 | 8 |

Example 5

The reaction was performed in the same manner as in Example 2-3 except that by using the same equipment as in Example 1, 600.0 g (2.47 mol) of 1-hexadecanol (produced by Kao Corporation, product name: Kalcol 6098), 8.7 g of a 48% potassium hydroxide aqueous solution (produced by Kanto Chemical Co., Inc.) as a base catalyst (potassium hydroxide: 0.12 mol/kg·1-hexadecanol, 3.0% by mol based on 1-hexadecanol), and 0.30 g of Cu—Fe—Al (produced by JGC Catalysts and Chemicals Ltd., product name: N2A3) as a co-catalyst (0.05% by mass based on 1-hexadecanol) were charged, and in the step 2, the time of holding at a constant temperature (constant holding time) was 60 minutes, and the raw material alcohol conversion and the Guerbet alcohol yield were quantitatively determined. The results are shown in Table 5.

Comparative Example 5

The reaction was performed in the same manner as in Example 5 except that the temperature rise was performed without temporal termination, i.e., the time of holding at a constant temperature (constant holding time) was 0 minute, and the raw material alcohol conversion and the Guerbet alcohol yield were quantitatively determined. The results are shown in Table 5.

TABLE 5

|  | Example 5 | Comparative Example 5 |
|---|---|---|
| Raw material alcohol | 1-hexadecanol | 1-hexadecanol |
| Co-catalyst | Cu—Fe—Al | Cu—Fe—Al |
| Co-catalyst amount (% by mass) | 0.05 | 0.05 |
| Constant holding temperature (° C.) | 150 | — |
| Constant holding time (min) | 60 | 0 |
| Water amount after holding at constant temperature (% by mass) | 0.26 | — |
| Holding time at 100° C. or more and 180° C. or less (min) | 98.6 | 68.6 |
| Water amount at 180° C. (% by mass) | 0.10 | 0.28 |
| Reaction temperature (° C.) | 240 | 240 |
| Reaction time (hr) | 4 | 4 |
| Raw material alcohol conversion (%) | 37 | 10 |
| Guerbet alcohol yield (%) | 15 | 6 |

Example 6

The reaction was performed in the same manner as in Example 1 except that in the step 2, the temperature was raised at 25° C./h from 100° C. to 150° C., and at 70° C./h from 150° C. to 180° C., and the raw material alcohol conversion and the Guerbet alcohol yield were quantitatively determined. The results are shown in Table 6.

TABLE 6

|  | Example 6 |
| --- | --- |
| Raw material alcohol | 1-dodecanol |
| Co-catalyst | Cu—Fe—Al |
| Co-catalyst amount (% by mass) | 0.01 |
| Holding time at 100° C. or more and 180° C. or less (min) | 164.4 |
| Water amount at 180° C. (% by mass) | 0.10 |
| Reaction temperature (° C.) | 240 |
| Reaction time (hr) | 3 |
| Raw material alcohol conversion (%) | 46 |
| Guerbet alcohol yield (%) | 40 |

INDUSTRIAL APPLICABILITY

The method for producing a Guerbet alcohol of the present invention enhances the conversion and the yield without the use of a solvent. The Guerbet alcohol obtained in the present invention can be favorably applied to a raw material, an intermediate material, or the like of a surfactant, a textile oil, a softening agent, a cosmetic product, a medical drug, a lubricating oil, and the like.

The invention claimed is:

1. A method for producing a Guerbet alcohol, comprising the following steps 1 to 3 in this order:
   step 1: preparing a liquid composition containing an aliphatic alcohol having a number of carbon atoms of 8 or more and 22 or less, and a base, wherein an amount of a solvent in said liquid composition is 5% by mass or less based on the aliphatic alcohol;
   step 2: holding the liquid composition at 100° C. or more and 150° C. or less under a gas stream for 70 minutes or more to 6.2 hours or less in order to thereby adjust a water amount in the liquid composition to less than 0.28% by mass; and
   step 3: setting the liquid composition to be more than 180° C. and holding the liquid composition at that temperature for 1 hour or more and 20 hours or less.

2. The method for producing a Guerbet alcohol according to claim 1, wherein the base is selected from the group consisting of an alkali metal hydroxide and an alkali metal alkoxide.

3. The method for producing a Guerbet alcohol according to claim 1, wherein the aliphatic alcohol is a saturated aliphatic alcohol having a number of carbon atoms of 8 or more and 22 or less.

4. The method for producing a Guerbet alcohol according to claim 1, wherein the liquid composition further contains a co-catalyst.

5. The method for producing a Guerbet alcohol according to claim 1, wherein the amount of the base is 0.3% by mol or more and 6.0% by mol or less based on the aliphatic alcohol.

6. The method for producing a Guerbet alcohol according to claim 1, wherein in the step 1, the temperature in preparing the liquid composition is 5° C. or more and less than 100° C.

7. The method for producing a Guerbet alcohol according to claim 1, wherein in the step 1, a pressure in preparing the liquid composition is ordinary pressure.

8. The method for producing a Guerbet alcohol according to claim 1, wherein a water amount in the aliphatic alcohol is 10% by mass or less.

9. The method for producing a Guerbet alcohol according to claim 1, wherein in the step 2, a pressure where the liquid composition is held at 100° C. or more and 150° C. or less is ordinary pressure.

10. The method for producing a Guerbet alcohol according to claim 1, wherein in the step 3, the temperature of the liquid composition is 190° C. or more.

* * * * *